US006880188B1

(12) United States Patent
Schmidt et al.

(10) Patent No.: US 6,880,188 B1
(45) Date of Patent: Apr. 19, 2005

(54) INFANT CARE APPARATUS WITH MOVABLE INFANT SUPPORT

(75) Inventors: Rick A. Schmidt, Orlando, FL (US); David C. Newkirk, Lawrenceburg, IN (US)

(73) Assignee: Draeger Medical Infant Care, Inc., Telford, PA (US)

( * ) Notice: Subject to any disclaimer, the term of this patent is extended or adjusted under 35 U.S.C. 154(b) by 0 days.

(21) Appl. No.: 10/149,539

(22) PCT Filed: Nov. 15, 2000

(86) PCT No.: PCT/US00/42181

§ 371 (c)(1),
(2), (4) Date: May 13, 2002

(87) PCT Pub. No.: WO01/43686

PCT Pub. Date: Jun. 21, 2001

Related U.S. Application Data

(60) Provisional application No. 60/165,623, filed on Nov. 15, 1999.

(51) Int. Cl.[7] ............................................... A61G 11/00
(52) U.S. Cl. ................. 5/603; 5/93.1; 600/22; 177/144
(58) Field of Search .................... 5/93.1, 93.2, 100, 5/603, 427, 430; 600/22; 128/205.26

(56) References Cited

U.S. PATENT DOCUMENTS

| 793,168 A | 6/1905 | Abrams |
|---|---|---|
| 1,787,805 A | 1/1931 | Walter |
| 1,914,288 A | 6/1933 | Poll, Sr. |
| 2,187,312 A | 1/1940 | Goodlake |
| 3,069,700 A | 12/1962 | Berlin |
| 3,158,150 A | 11/1964 | Croasdaile |
| 3,187,744 A | 6/1965 | Dorsak et al. |
| 3,387,600 A | 6/1968 | Terzian |
| 3,511,162 A | 5/1970 | Truhan |
| 3,618,734 A | 11/1971 | Khan |
| 3,776,217 A | 12/1973 | van Galen et al. |
| 3,782,362 A | 1/1974 | Puzio |
| 3,821,947 A | 7/1974 | Schossow |
| 3,858,570 A | 1/1975 | Beld et al. |
| 4,063,495 A | 12/1977 | Duvlis |

(Continued)

FOREIGN PATENT DOCUMENTS

| DE | 20 61 704 | 6/1971 |
|---|---|---|
| DE | 36 07 575 | 9/1987 |
| EP | 0 236 851 | 9/1987 |
| FR | 2 031 559 | 11/1970 |
| GB | 1 232 048 | 5/1971 |
| GB | 2 067 077 | 7/1981 |
| GB | 2 175 213 | 11/1986 |
| JP | 122184 | 11/1974 |
| JP | 103817 | 4/1993 |
| WO | WO 83/01189 | 4/1983 |
| WO | WO 90/09771 | 9/1990 |
| WO | WO 97/11664 | 4/1997 |

OTHER PUBLICATIONS

Musch, Adams and Sunshine, *Journal of Pediatrics*, "Air Curtain Incubator for use in Intensive–Care Nursery," vol. 79., No. 6, pp. 1024–1030.

(Continued)

*Primary Examiner*—Michael Trettel
(74) *Attorney, Agent, or Firm*—Caesar, Rivise, Bernstein, Cohen & Pokotilow, Ltd.

(57) ABSTRACT

An infant-support apparatus for an incubator or warmer. The apparatus comprises a frame and an infant supporting deck having a central position relative to the frame. The deck is movable relative to the frame to laterally extended positions away from the central position.

31 Claims, 12 Drawing Sheets

U.S. PATENT DOCUMENTS

| | | |
|---|---|---|
| 4,140,105 A | 2/1979 | Duvlis |
| 4,161,172 A | 7/1979 | Pickering |
| 4,186,456 A | 2/1980 | Huempfner |
| 4,222,602 A | 9/1980 | Kouth |
| 4,321,913 A | 3/1982 | Maluta et al. |
| 4,361,137 A | 11/1982 | Grosholz |
| 4,423,669 A | 1/1984 | Bullock et al. |
| 4,552,034 A | 11/1985 | Bertani et al. |
| 4,617,912 A | 10/1986 | Beer et al. |
| 4,628,553 A | 12/1986 | Buttitta et al. |
| 4,641,385 A | 2/1987 | Peters et al. |
| 4,734,945 A | 4/1988 | Wright |
| 4,750,474 A | 6/1988 | Dukhan |
| 4,773,392 A | 9/1988 | Koch |
| 4,796,605 A | 1/1989 | Sasaki et al. |
| 4,809,677 A | 3/1989 | Mackin et al. |
| 4,819,282 A | 4/1989 | McArthur et al. |
| 4,846,783 A | 7/1989 | Koch et al. |
| 4,885,918 A | 12/1989 | Vaccaro |
| 4,934,007 A | 6/1990 | Sweet |
| 4,936,824 A | 6/1990 | Koch et al. |
| 5,112,293 A | 5/1992 | Vaccaro |
| 5,119,467 A | 6/1992 | Barsky et al. |
| 5,162,038 A | 11/1992 | Wilker |
| 5,224,923 A | 7/1993 | Moffett et al. |
| 5,242,375 A | 9/1993 | McDonough |
| 5,244,452 A | 9/1993 | Vaccaro et al. |
| 5,285,054 A | 2/1994 | Barsky |
| 5,285,519 A | 2/1994 | Barsky et al. |
| 5,308,310 A | 5/1994 | Roff et al. |
| 5,316,542 A | 5/1994 | Koch et al. |
| 5,330,415 A | 7/1994 | Storti et al. |
| 5,336,156 A | 8/1994 | Miller et al. |
| 5,339,223 A | 8/1994 | Kremenchugsky et al. |
| 5,352,869 A | 10/1994 | Barsky |
| 5,376,761 A | 12/1994 | Koch et al. |
| 5,400,425 A | 3/1995 | Nicholas et al. |
| 5,446,934 A | 9/1995 | Frazier |
| 5,453,077 A | 9/1995 | Donnelly et al. |
| 5,474,517 A | 12/1995 | Falk et al. |
| 5,498,229 A | 3/1996 | Barsky et al. |
| 5,531,663 A | 7/1996 | Gloyd et al. |
| 5,539,854 A | 7/1996 | Jones et al. |
| D375,792 S | 11/1996 | Hillman et al. |
| 5,616,115 A | 4/1997 | Gloyd et al. |
| 5,624,375 A | 4/1997 | Dykes et al. |
| 5,649,896 A | 7/1997 | Barsky |
| 5,759,149 A | 6/1998 | Goldberg et al. |
| 5,800,335 A | 9/1998 | Koch et al. |
| 5,817,002 A | 10/1998 | Donnelly et al. |
| 5,817,003 A | 10/1998 | Moll et al. |
| 5,830,123 A | 11/1998 | Franz et al. |
| 5,876,323 A | 3/1999 | Hodge et al. |
| 5,971,913 A | 10/1999 | Newkirk et al. |
| 5,971,914 A | 10/1999 | Donnelly et al. |
| 6,022,310 A | 2/2000 | Goldberg et al. |
| 6,024,694 A | 2/2000 | Goldberg et al. |
| 6,036,634 A | 3/2000 | Goldberg et al. |
| 6,049,924 A | 4/2000 | Prows et al. |
| 6,071,228 A | 6/2000 | Speraw et al. |

OTHER PUBLICATIONS

"Infa–Care 2000," Infa–Care, Inc. Product Brochure, six pages, 1972.

"Stabilet® From Hill–Rom®" Product Brochure, six pages, 1992.

"Stabilet CC™ From Hill–Rom®" Product Brochure, six pages, 1992.

"The Stabilet™ Freestanding Warmer and Clinical Bassinet From Hill–Rom®" Product Brochure, four pages, 1993.

"'A Hill–Rom Solution;' Stabilet 2000C, Stabilet CC; Stabilet Freestanding Infant Warmer Accessories" Product Borchure, eight pages, 1995.

"ISOLETTE® Infant Incubator . . . The Essence of Incubation," Air–Shields, Inc. Product Brochure, eight pages, 1996.

"The New Isolette® Infant Incubator Only from Air–Shields" Product Brochure, one page, Sep. 1996.

INFANT CARE APPARATUS WITH MOVABLE INFANT SUPPORT

RELATED APPLICATION

This application is a U.S. national counterpart application of international application Ser. No. PCT/US00/42181 filed Nov. 15, 2000, which claims priority to U.S. application Ser. No. 60/165,623 filed Nov. 15, 1999.

TECHNICAL FIELD

The present invention relates to infant support apparatus for use as infant-care units of the type having a movable infant support.

BACKGROUND AND SUMMARY

Infant care units, such as an infant incubator or warmer that includes various systems for controlling the temperature and humidity to facilitate the development of a premature infant, are known. Such incubators conventionally include an infant support surface for supporting the infant and some type of overhead structure, such as a canopy, above the infant support surface. In some cases, an isolation chamber is formed by a set of panels arranged around the infant support surface. The canopy cooperates with these panels to enclose the isolation chamber.

It is typical in such systems to provide access to the infant. For example, panels may be provided with access openings through which care givers gain access to the infant. Such units may also include canopies that have access doors to provide further access to the infant. It is also known for the canopies of such units to be movable away from the infant support surface and for the panels of such units to be movable away from the infant support surface to provide still further access to the infant.

Incubators are also known to include an infant support surface or deck that may be tilted relative to the incubator for moving the infant to a desirable position for treatment. For example, the deck can be moved to Trendelenberg or reverse-Trendelenberg tilted positions. To accommodate this movement, the deck is often suspended above a tub or frame having a cavity disposed therein. When moved to one of these positions, a portion of the deck extends into the cavity. In such instances, the cavity must be sized to provide sufficient space to allow this broad range of tilted positions. The cavity is also useful for receiving scales and x-ray cassette trays which are often positioned below the deck.

It would be beneficial to further improve a care givers access to the infant. It would also be beneficial to provide convenient access to the cavity for maintenance of the apparatus and cleaning the cavity.

According to the present invention an infant support apparatus comprising a frame and an infant supporting deck is provided. The infant supporting deck is movable relative to the frame between a central position and at least one extended position away from the central position.

The preferred embodiment further includes a mounting mechanism configured to secure the deck to the frame. The mounting mechanism mounts the deck to the frame and permits movement of the deck relative to the frame between at least one extended position and the central position. The preferred mounting mechanism includes first and second slide assemblies, first and second bearing surfaces, rails, a projecting pin and a pin-receiving aperture, a weldment, a scale, and an x-ray cassette.

The preferred embodiment of the present disclosure provides an infant support apparatus having a deck which is movable between a central position and a position spaced therefrom in a plane parallel to a plane defined by the infant support surface. The preferred embodiment includes a cavity wherein the deck substantially covers and hides the cavity when the deck is in the central position. The deck is configured to expose the cavity when the deck is in a position spaced from the central position.

The preferred embodiment of the present disclosure provides an infant support apparatus comprising a base carrying a support configured to receive an infant. Side guards are provided which are associated with the support. The side guards are also movable between upright and lowered positions and are configured to provide access to the infant. An assembly is provided comprising a canopy and a radiant warmer. The assembly is movable upwardly and downwardly relative to the support between upper and lower positions. When the assembly is in the lower position, the canopy cooperates with the side guards, in the upright position, to form an incubator enclosure configured to receive the infant. When the assembly is in the upper position, the radiant warmer provides warmth to the infant. Further illustrative embodiments include a humidifier for providing moist air to the enclosure. An x-ray tray under the support surface, and one or more weight scales may also be provided.

Additional features and advantages of the apparatus will become apparent to those skilled in the art upon consideration of the following detailed descriptions exemplifying the best mode of carrying out the apparatus as presently perceived.

BRIEF DESCRIPTION OF THE DRAWINGS

The illustrative apparatus will be described hereinafter with reference to the attached drawings, which are given as non-limiting examples only, in which.

Corresponding reference characters indicate corresponding parts throughout the several views. The exemplification set out herein illustrates several embodiments of the apparatus, and such exemplification is not to be construed as limiting the scope of the apparatus in any manner.

DETAILED DESCRIPTION OF THE DRAWINGS

An infant support apparatus 120 in accordance with the present invention includes a base 122 carrying an infant support 126 as shown, for example, in FIGS. 1–7. Infant support 126 includes side panels 144 that may be positioned in a raised position, as shown, for example, in FIGS. 1–4, or in a lowered position, as shown, for example, in FIGS. 5–7 in which side panels 144 do not obstruct access of a care giver (not shown) to an infant 200 resting on an infant supporting deck 21. One mechanism for mounting side panels so that they may be moved between the raised position and the lowered position is disclosed in U.S. Pat. No. 6,049,924, the disclosure of which is hereby incorporated by reference.

Figure 1:
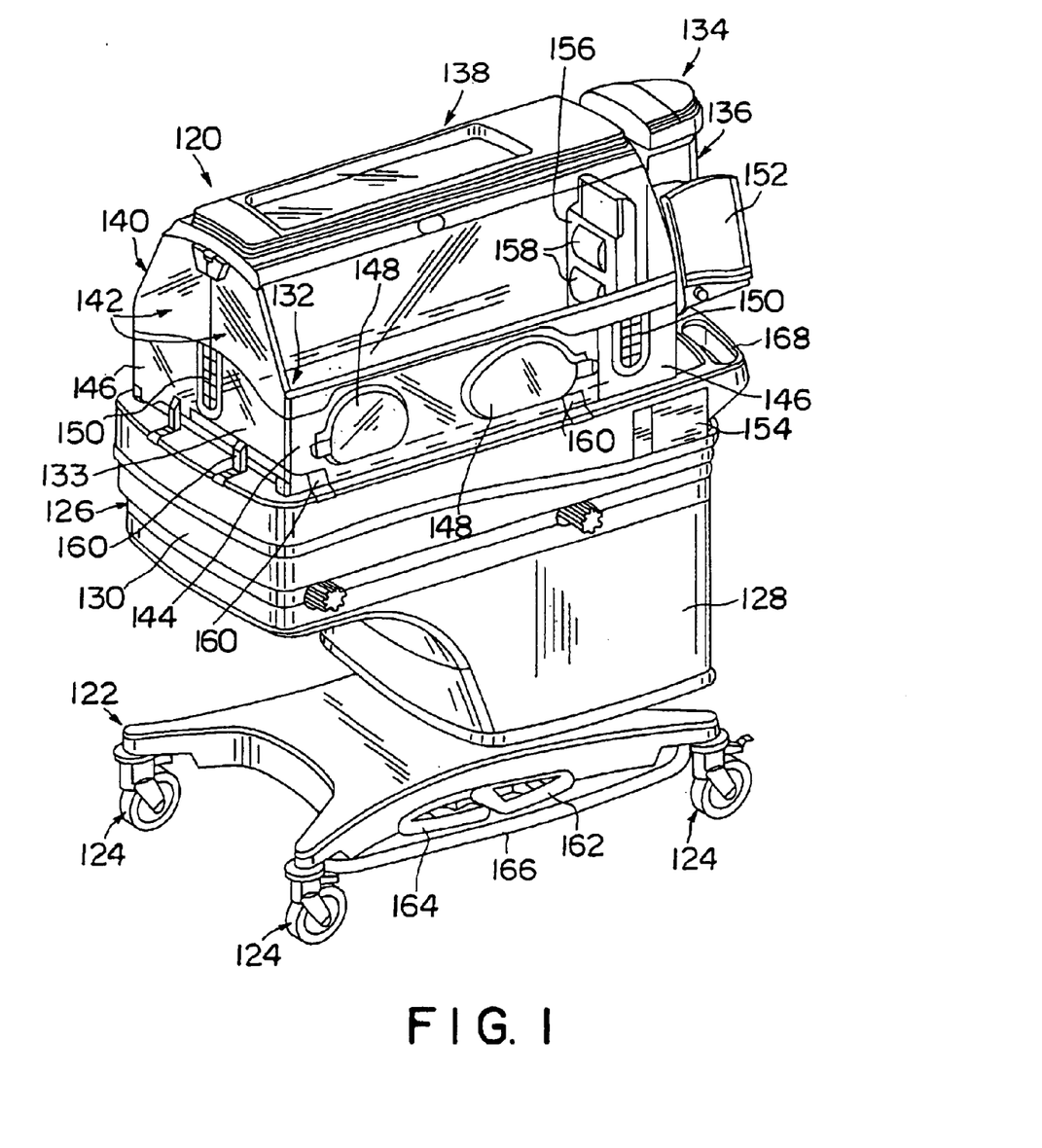
FIG. 1 is a perspective view of an infant support apparatus.
Figure 2:
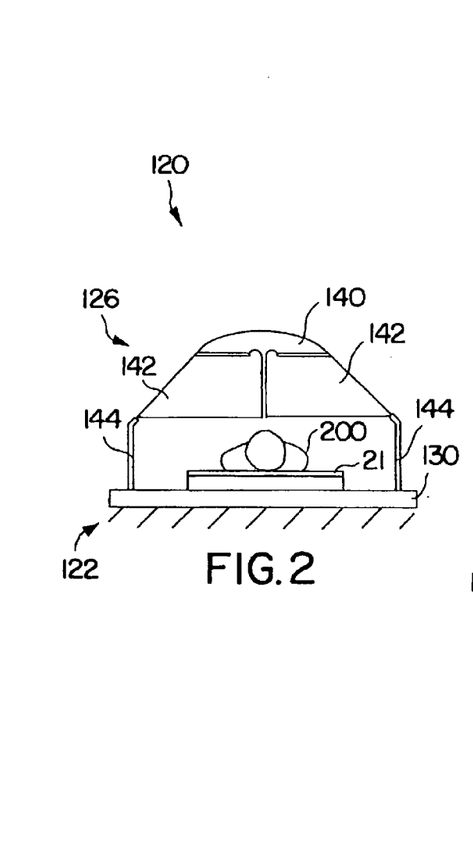
FIG. 2 is a diagrammatic end view of the infant support apparatus of FIG. 1 showing side panels in the raised position, the canopy lowered to its lowered position, and the canopy halves positioned in their respective lowered positions, the side panels and the canopy halves cooperating with a frame and an infant supporting deck to enclose an infant.
Figure 3:
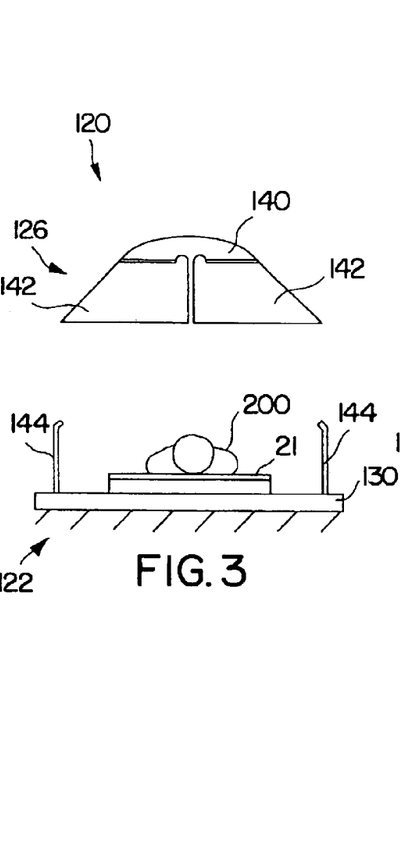
FIG. 3 is a view of the infant support apparatus similar to FIG. 2 showing the canopy moved to its raised position providing a care giver (not shown) with access to the infant.
Figure 4:
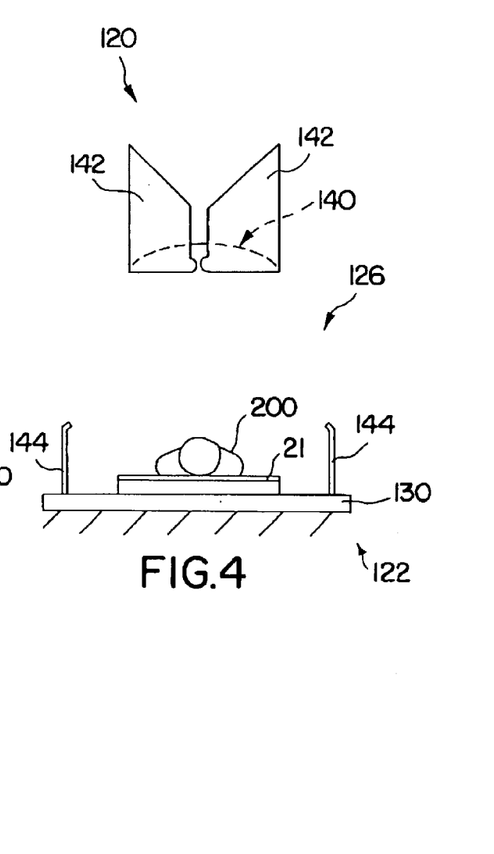
FIG. 4 is a view similar to FIG. 2, showing the canopy at its raised position and the canopy halves rotated to their respective raised positions providing a care giver (not shown) with access to the infant.

Infant support apparatus 120 is provided with a canopy 140 that is movable between a lowered position shown, for example, in FIGS. 1 and 2, in which canopy 140 cooperates with side panels 144, a frame 130, and an infant supporting deck 21 to enclose infant 200, and a raised position spaced apart from side panels 144, as shown, for example in FIGS. 3–7, when canopy 140 is in the raised position, the care giver may access infant 200 through the opening formed between side panels 144 and canopy 140.

Canopy 140 includes first and second canopy halves 142 as shown, for example, in FIGS. 2–7 and FIGS. 8 and 9. In preferred embodiments, canopy halves 140 are individually movable between lowered positions, shown, for example, in FIGS. 1–3 and 8, and raised positions, as shown, for example, in FIGS. 4–7 and 9. It will be appreciated by those skilled in the art that the care giver obtains greater access to infant 200 when canopy halves 142 are in the raised position.

Infant support 126 includes frame 130 carrying infant supporting deck 21. Infant supporting deck 21 is mounted to frame 130 for movement relative to frame 130 between a first position, as shown, for example, in FIG. 6, and a second position, as shown, for example, in FIG. 7. In preferred embodiments, the first position of deck 21 is spaced apart from a central position of deck 21 generally centered on frame 130, as shown, for example, in FIGS. 2–5. Additionally, in preferred embodiments, the second position of deck 21 is spaced apart from the central position of deck 21. Thus, in preferred embodiments, deck 21 slides from the central position to either side of the infant support apparatus. However, it is within the scope of this disclosure for either the first position or the second position of deck 21 to be the central position so that deck 21 is movable to only one side of infant support apparatus 120.

It will be appreciated by those skilled in the art that infant support apparatus 120 will provide a care giver with improved access to infant 200 when side panels 144 are in their lowered positions, canopy 140 is in the raised position, canopy halves 142 are in their raised positions, and deck 21 is slid to either its first or second position adjacent the care giver. It will also be appreciated by those skilled in the art that with canopy 140 in the lowered position, or canopy halves 142 in their respective lowered positions, the care giver's access to infant 200 will still be enhanced by sliding deck 21 toward the care giver.

Figure 5:
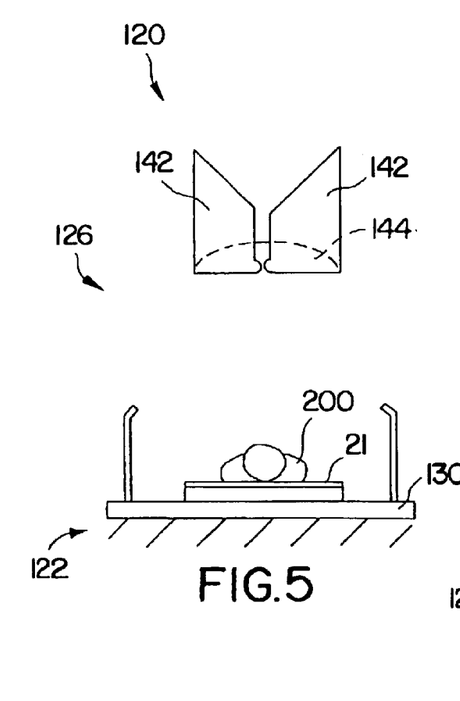
FIG. 5 is a view similar to FIG. 4 showing the side panels in their respective lowered positions providing a care giver (not shown) with still greater access to the infant.
Figure 6:
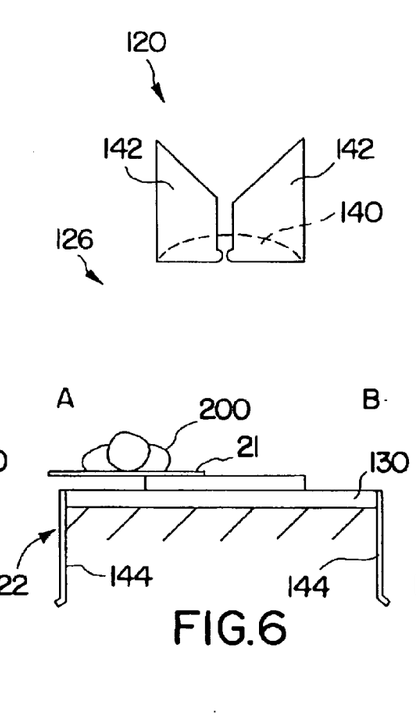
FIG. 6 is a view similar to FIG. 4 showing the infant supporting deck slid toward side A of the infant support apparatus, providing a care giver (not shown) with additional access to the infant.

Thus, a care giver standing adjacent side A of infant support apparatus 120 as shown, for example, in FIG. 6, will have improved access to infant 200 when deck 21 is slid from the central position of deck 21, shown in FIG. 5, to the first position of deck 21 shown in FIG. 6. Likewise, a care giver standing adjacent side B of the infant support apparatus 120 as shown, for example, in FIG. 7 will have improved access to infant 200 when deck 21 is slid from the central position of deck 21, shown, for example, in FIG. 5, to the second position of deck 21, shown, for example in FIG. 6.

Infant support apparatus 120 in accordance with the present invention, as shown, for example, in FIGS. 2–7, includes frame 130 and infant supporting deck 21 carried by frame 130. Infant supporting deck 21 is movable relative to frame 130 between a first position and a second position spaced apart from the first position. A preferred embodiment of infant support apparatus 120 is described in more detail in FIGS. 1 and 8–19.

Figure 17:
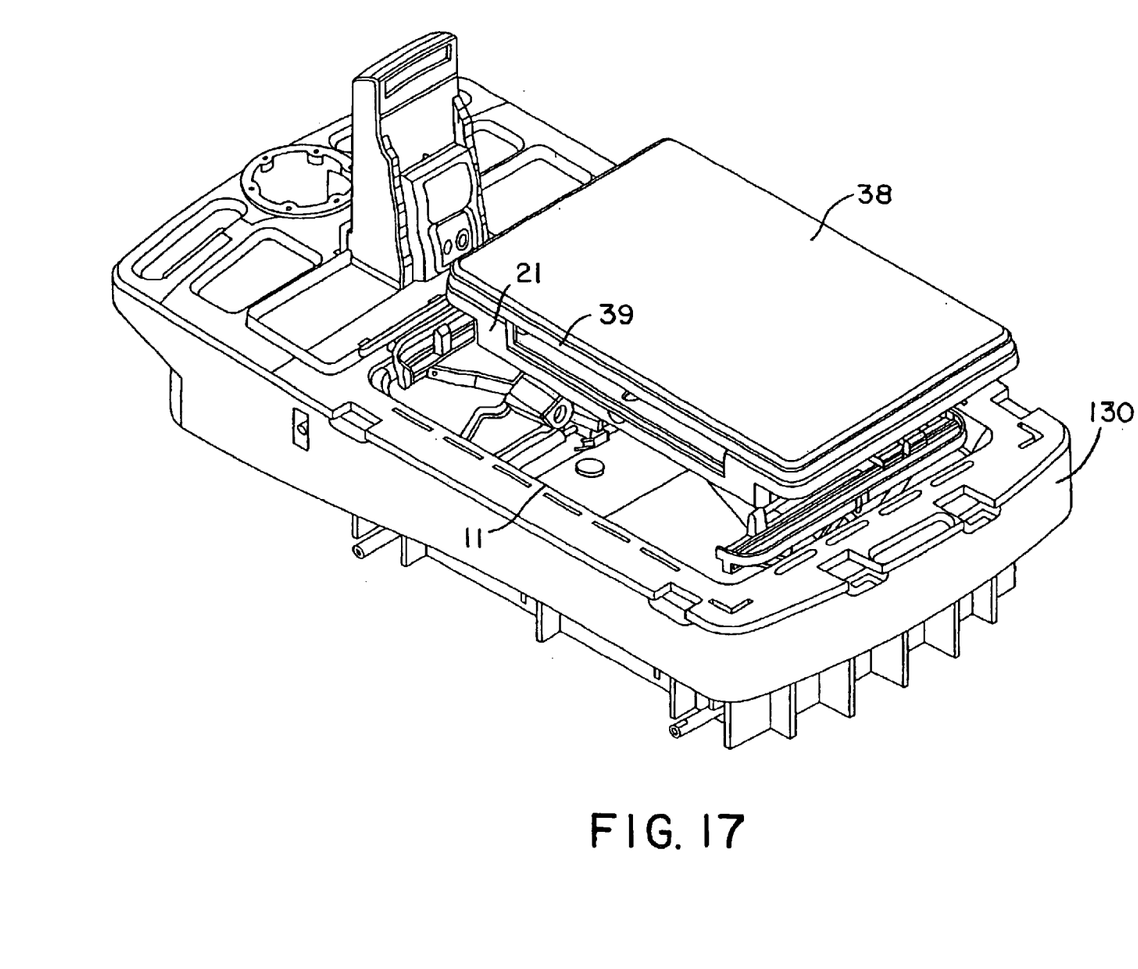
FIG. 17 is another perspective view of a portion of the infant support apparatus of FIG. 1 showing the deck moved to an extended position spaced apart from a central position.

According to the preferred embodiment of infant support apparatus 120, deck 21 or associated structure upon which an infant is supported is provided. Deck 21 is movable laterally with respect to apparatus 120 between a central position shown, for example, in FIG. 17 and a laterally extended position shown, for example, in FIG. 16. In such laterally extended positions, deck 21 remains in substantially the same plane as it occupies when in the central position. It is contemplated that the laterally extended position exists in any direction that is spaced apart from the central position, as shown in FIG. 17, and is not limited to the illustrated extended position, which is shown for illustrative purposes only.

Infant support apparatus 120, such as an infant warming device or incubator, includes a base 122, a plurality of castors 124 extending downwardly from base 122, and an infant supporting portion or infant support 126 supported above base 122, as shown in FIG. 1. Infant support 126 includes a pedestal 128 coupled to base 122 for vertical movement, a platform tub 130 supported by pedestal 128, and a mattress 132 supported above platform tub 130. Mattress 132 has an upwardly facing infant support surface 133. Infant support apparatus 120 also includes a canopy support arm 134 including a telescoping vertical arm 136 connected to a horizontal overhead arm 138. A canopy 140 is coupled to overhead arm 138, and is positioned to lie above platform tub 130. Canopy 140 includes a pair of canopy halves 142 coupled to overhead arm 138 for pivoting movement between a lowered position, shown, for example, in FIGS. 1 and 9, and a raised position, shown in FIG. 10.

A pair of transparent side guard panels 144 and a pair of transparent end guard panels 146 extend upwardly from platform tub 130, as shown in FIG. 1. Side guard panels 144 and end guard panels 146 cooperate with canopy halves 142 and overhead arm 138 to provide infant support apparatus 120 with an isolation chamber. Side guard panels 144 may be formed to include a pair of access ports that are normally closed by access port covers 148. A care giver may open access port covers 148 to gain limited access to an infant supported by infant support apparatus 120. Each end guard panel 146 is formed to include at least one U-shaped window. A pass-through grommet 150 is positioned to lie in each U-shaped window. Wires and tubes (not shown) can be routed into the isolation chamber through pass-through grommets 150.

Infant support apparatus 120 includes a user interface panel 152 for monitoring various systems that control the temperature and humidity of the isolation chamber, and for allowing care givers to input various control parameters into memory of a control system of infant support apparatus 120, as shown in FIG. 1. Infant support apparatus 120 also includes a humidifier module 154 that can be filled with water and inserted into a humidifier compartment of platform tub 130. Heated air is blown through humidifier module 154 and directed into the isolation chamber.

A tower 156 is positioned to lie in the isolation chamber. Tower 156 supports various sensors 158, such as patient environmental sensors and light and noise sensors, and also provides a return-air path for the air being circulated through the isolation chamber.

Hinges 160 are provided as shown in FIG. 1 so that side guard panels 144 and one of end guard panels 146 can pivot downwardly away from canopy 140 to provide increased access to the infant supported by infant support apparatus 120. Controls (not shown) can be activated to extend and retract vertical arm 136 of canopy support arm 134, thereby raising and lowering, respectively, overhead arm 138 and canopy 140. It will be appreciated by those skilled in the art that lowering canopy 140 provides advantages of an isolation chamber while decreasing the care giver's access to the infant while raising canopy 140 provides the care givers with greater access to the infant.

Figure 8:
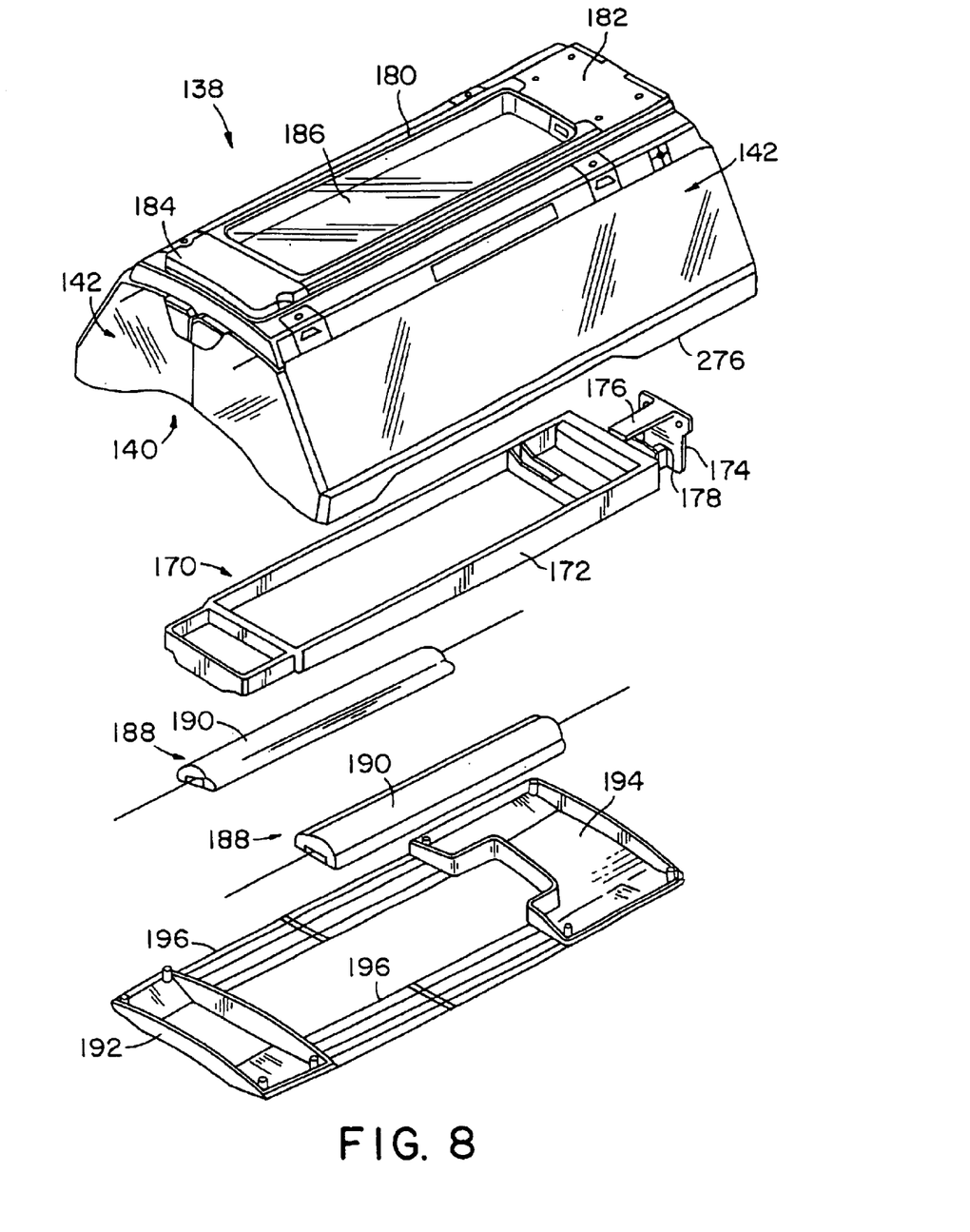
FIG. 8 is an exploded view of a portion of the canopy support arm of the apparatus of FIG. 1.

Overhead arm 138 includes an overhead arm structural member 170 having a substantially rectangular frame member 172 and an end plate 174 coupled to frame member 172 by a horizontal flange 176 and a vertical flange 178, as shown in FIG. 8. Overhead arm structural member 170 supports other components of overhead arm 138. A top cover 180 overlies structural member 170 and is attached thereto. Canopy halves 142 are attached to top cover 180 for pivoting movement relative to overhead arm 138 and relative to one another. In addition, overhead arm 138 includes a circuit board cover 182 that covers an electrical circuit (not shown) situated in a rear compartment formed in top cover 180, and an alarm light cover 184 that covers a set of alarm lights (not shown) situated in a front compartment formed in top cover 180. Overhead arm 138 includes an elongated x-ray window 186 received in a central aperture formed in top cover 180.

A pair of infrared heater assemblies 188 are coupled to overheard arm 138 below overhead arm structural member 170 as shown in FIG. 8. Infrared heater assemblies 188 provide warmth to the patient supported on infant support surface 133. Infrared heater assemblies 188 extend longitudinally and are laterally spaced apart from one another as shown in FIG. 2. Each infrared heater assembly 188 includes a deflector 190 to direct the heat towards infant support 126. Overhead arm 138 includes a front bottom cover 192 and a rear bottom cover 194, each of which couple to top cover 180. A pair of heater grills 196 are connected to and extend longitudinally between front and rear bottom covers 192, 194 beneath infrared heater assemblies 188.

Infant support apparatus 120 includes a third heater (not shown) positioned to lie in tub 130 which heats air that is circulated beneath canopy 140 by an air circulation system (not shown) of the infant support apparatus 120. Humidifier module 154 also includes a heater to heat the water contained therein so that, as the heated air is circulated through humidifier module 154, the air is humidified. The heated air is directed upwardly adjacent to the side and end panels 144, 146, and is deflected by canopy 140 over infant support surface 133. By properly aligning canopy 140 with side and end guard panels 144, 146, convective heat losses and air losses are minimized.

Figure 9:
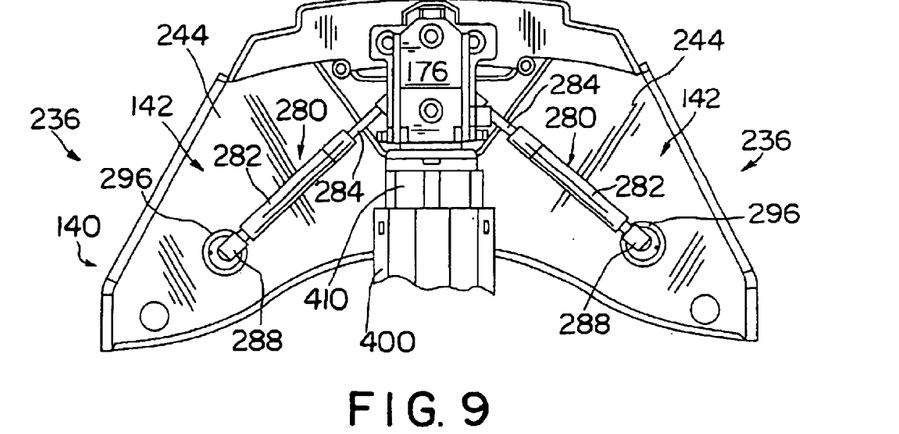
FIG. 9 is an end elevation view of an attachment mechanism, overhead arm and canopy halves from the apparatus of FIG. 1 showing the canopy halves in a lowered position.
Figure 10:
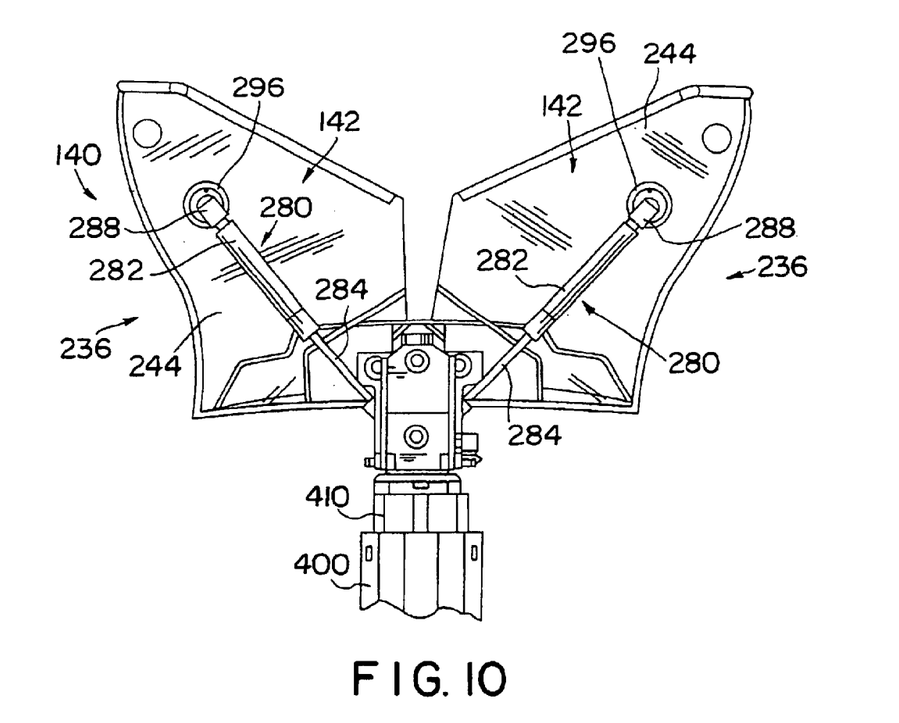
FIG. 10 is an end elevation view similar to FIG. 8 showing the canopy halves in a raised position.

A first gas spring dashpot 280, couples one canopy half 142 to overhead arm 138, and a second gas spring dashpot 280 couples the other canopy half 142 to overhead arm 138, as shown in FIGS. 9 and 10. When canopy halves 142 are in the lowered position, gas spring dashpots 280 are in retracted positions, shown in FIG. 9, and when canopy halves 142 are in the raised position, gas spring dashpots 280 are in extended positions, shown in FIG. 10. Gas spring dashpots 280 urge canopy halves 142 toward their respective raised positions, and to restrict inadvertent movement of canopy halves 142 relative to overhead arm 138 while in the raised and lowered positions.

Canopy support arm 134 includes vertical arm 136 and overhead arm 138 as previously described as shown in FIGS. 9 and 10. Vertical arm 136 includes an outer tubular column 400, an inner tubular column 410, and a telescoping drive assembly (not shown). Inner column 410 telescopically extends and retracts relative to outer column 400 in response to actuation of the drive assembly to raise and lower canopy halves 142.

Other features of the infant support apparatus 120 are discussed in detail in, and may be constructed and operated in accordance with, those apparatus shown and described in U.S. Pat. No. 6,071,228, entitled PATIENT-SUPPORT ASSEMBLY FOR THERMAL SUPPORT APPARATUS, the disclosure of which is hereby incorporated by reference. Other features of the infant support apparatus are discussed in detail in U.S. Pat. No. 6,022,310, entitled CANOPY ADJUSTMENT MECHANISMS FOR THERMAL SUPPORT APPARATUS; U.S. Pat. No. 6,049,924, entitled HINGED PANELS FOR A THERMAL SUPPORT APPARATUS; and U.S. Pat. No. 6,024,694, entitled HUMIDIFIER FOR A THERMAL SUPPORT APPARATUS, each of which is also incorporated herein by reference.

Figure 11:
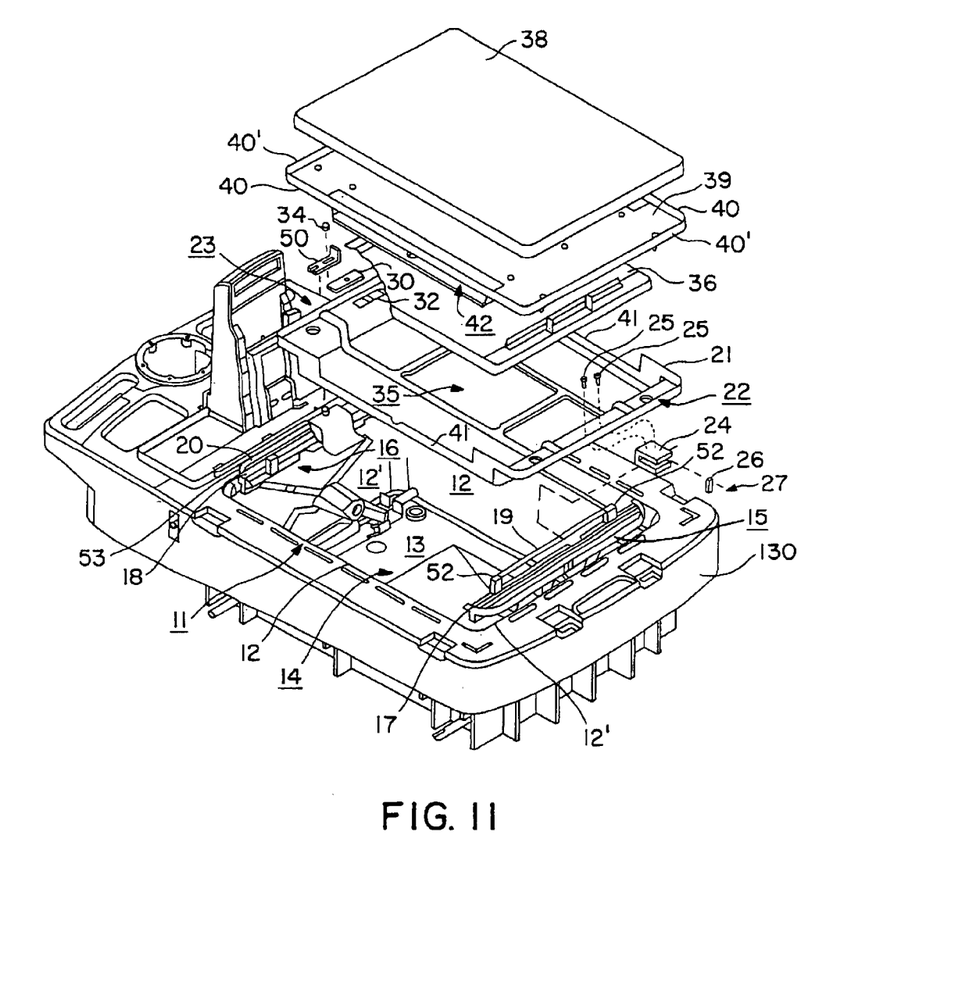
FIG. 11 is an exploded perspective view of a portion of the infant support apparatus of FIG. 1.

As shown in FIG. 11, tub 130 comprises a frame 11 defined by spaced side and end walls 12, 12' appending from bottom 13 to form a cavity 14. Attached at opposite ends of bottom 13 are first and second mounting mechanisms 15, 16. First and second mounting mechanisms 15, 16 are configured to couple deck 21 to tub 130, suspending deck 21 at a central position over cavity 14. First and second rail supports 17, 18 are attached to first and second mounting mechanisms 15, 16, respectively. First and second rails 19, 20 are attached to first and second rail supports 17, 18, respectively. These supports and rails allow deck 21, and mattress 38 carried by deck 21 to be raised and lowered with respect to frame 11, as described further herein. It is appreciated that any variety of structures that can raise and lower mattress 38 relative to frame 11 may be used in place of rail supports 17, 18 and rails 19, 20. For example, tilting, pivoting, or swinging mechanisms can be used to move mattress 38 relative to frame 11.

Figure 7:
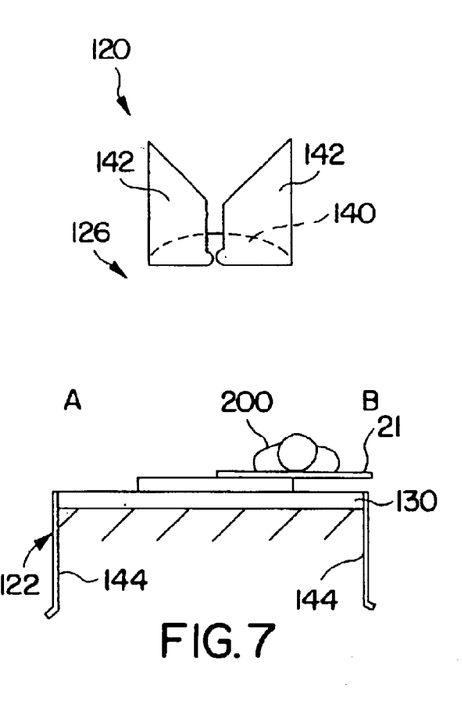
FIG. 7 is a view similar to FIG. 4 showing the infant supporting deck slid toward side B of the infant support apparatus, providing a care giver (not shown) on side B of the infant support apparatus with additional access to the infant.
Figure 12:
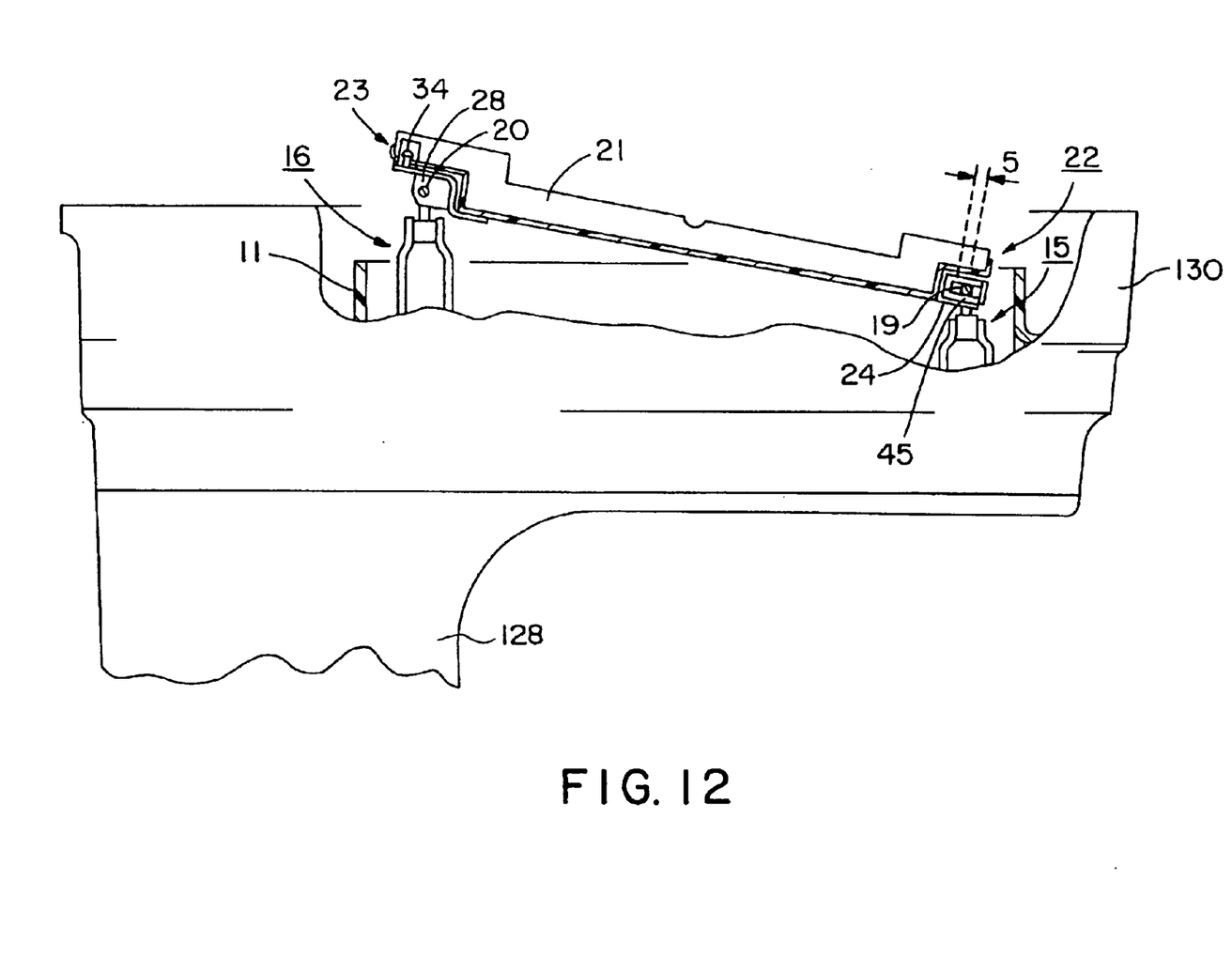
FIG. 12 is a side elevation view of the infant support apparatus of FIG. 1 with portions broken away showing the deck in a Trendelenberg tilt position.
Figure 18:
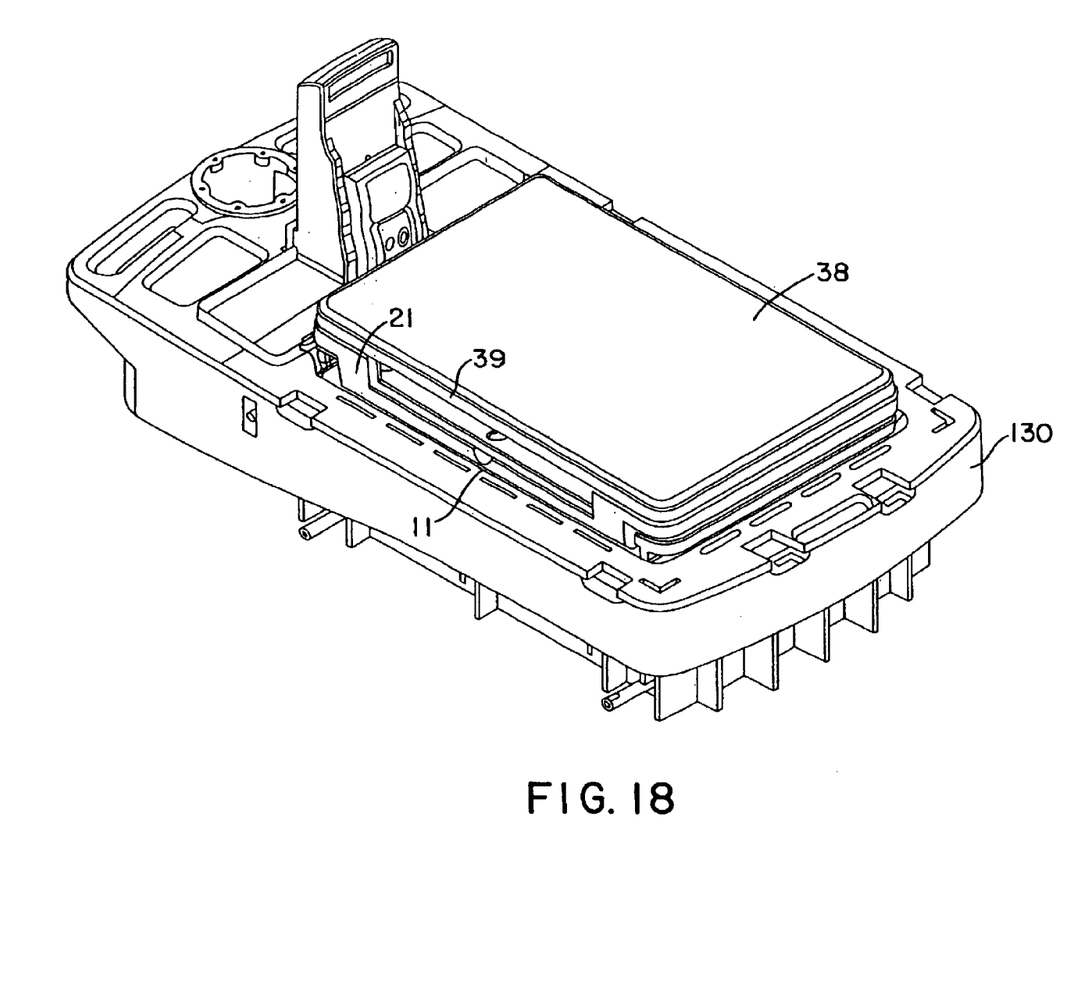
FIG. 18 is still another perspective view of a portion of the infant support apparatus of FIG. 1 showing the deck in the central position.
Figure 19:
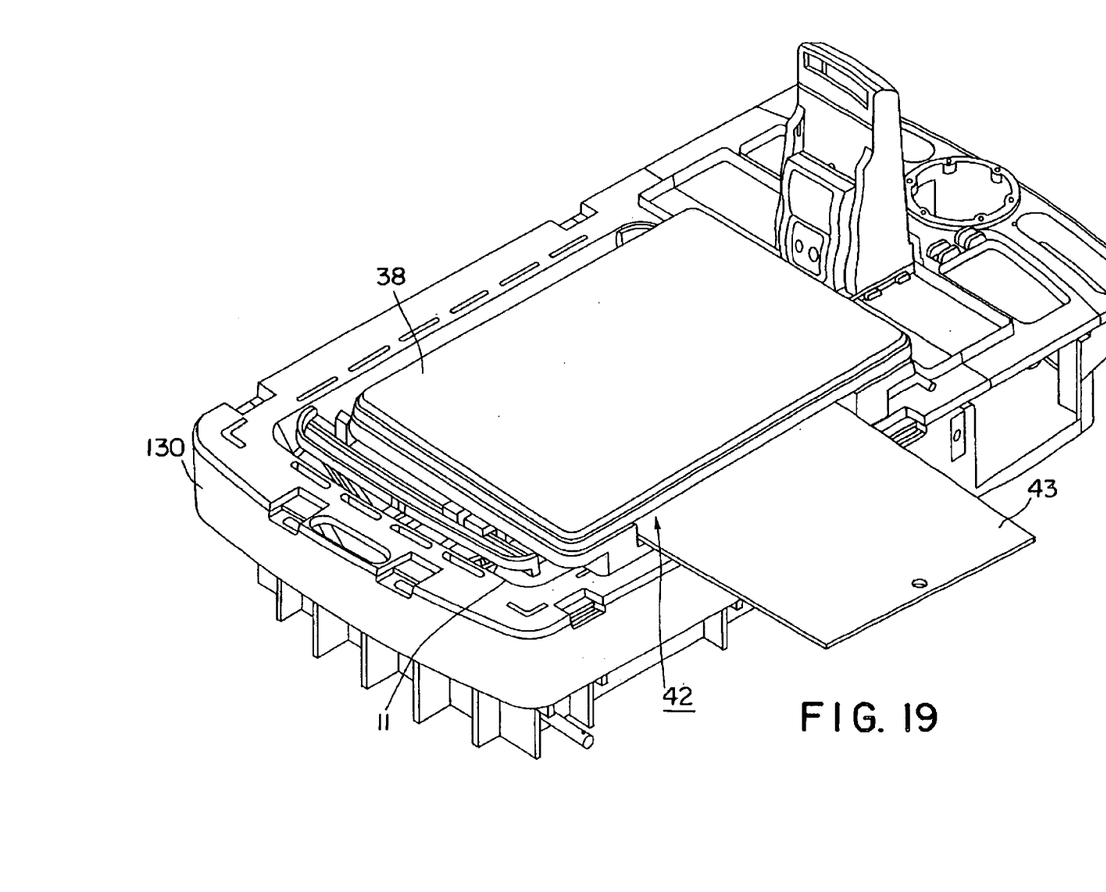
FIG. 19 is a perspective view of a portion of the infant support apparatus of FIG. 1 showing the deck moved to the extended position and an x-ray tray extended from the deck.

Deck 21 is oriented in a central position relative to frame 11, as shown in FIG. 18. Deck 21 is movable between the extended position as shown in FIGS. 6, 7 and 17, and the central position. It is appreciated, however, that deck 21 may be configured to move between any positions on the same general plane defined by deck 21. Deck 21 also has longitudinally spaced apart first and second ends 22, 23, as shown in FIGS. 11 and 12. A recess 35 is formed in deck 21 sized to accept a scale 36 for weighing an infant. (See also FIGS. 13 and 19.) Above recess 35, mattress tray 39 is positioned on top surfaces 37, 37' of deck 21. Mattress tray 39 includes laterally spaced-apart sides 40, 40' configured to receive mattress 38. A slot 42 is provided underneath mattress tray 39 so that an x-ray cassette 43 can be inserted from either side of mattress tray 39. (See FIG. 13.) A weldment 44 is also provided and is configured to attach to deck 21. Weldment 44 is a rigid frame structure that provides support for infant 200 lying on mattress 38.

Figures 13, 14:
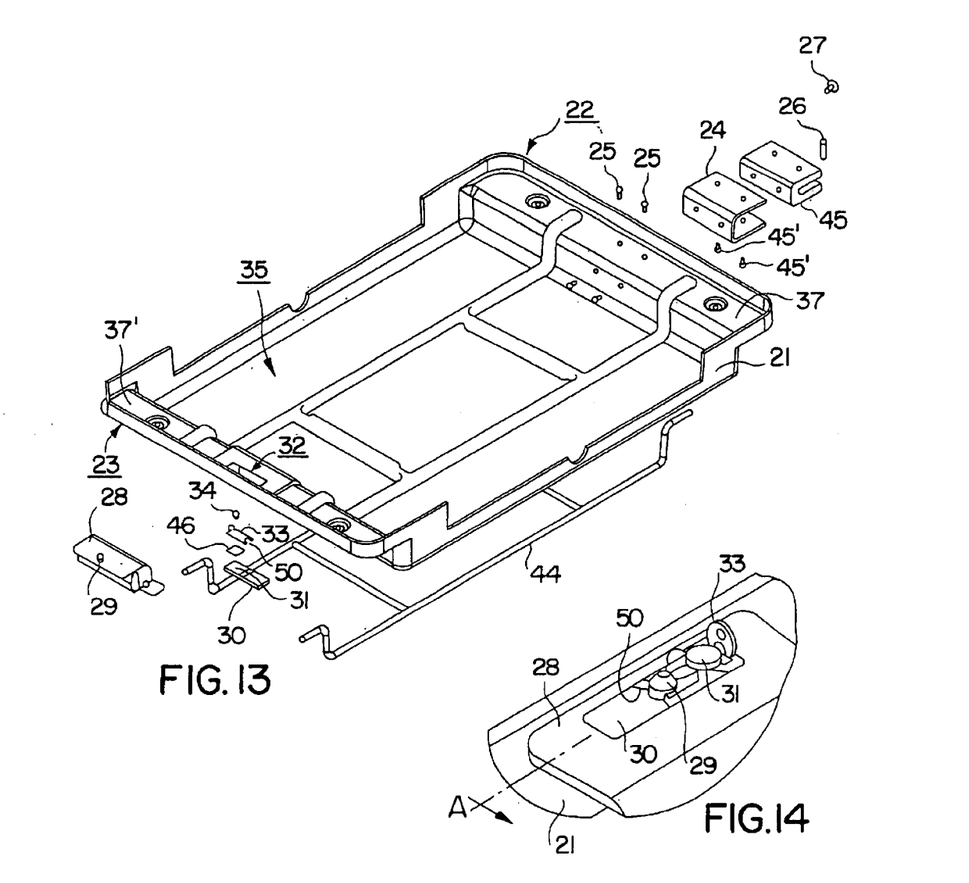
FIG. 13 is an exploded perspective view of a portion of the deck of the infant support apparatus of FIG. 11 showing the slide bracket and pivot mount assembly.
FIG. 14 is a perspective view of a portion of the infant support apparatus of FIG. 1 showing the pivot mount assembly from FIG. 13 coupled to the deck.
Figure 15:
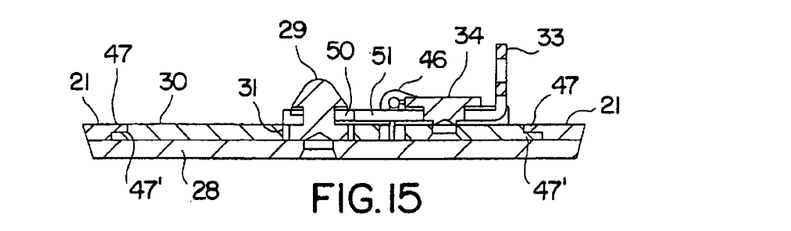
FIG. 15 is a sectional view of a portion of the infant support apparatus taken along line A—A of FIG. 13 showing the pivot mount assembly coupled to the deck.
Figure 16:
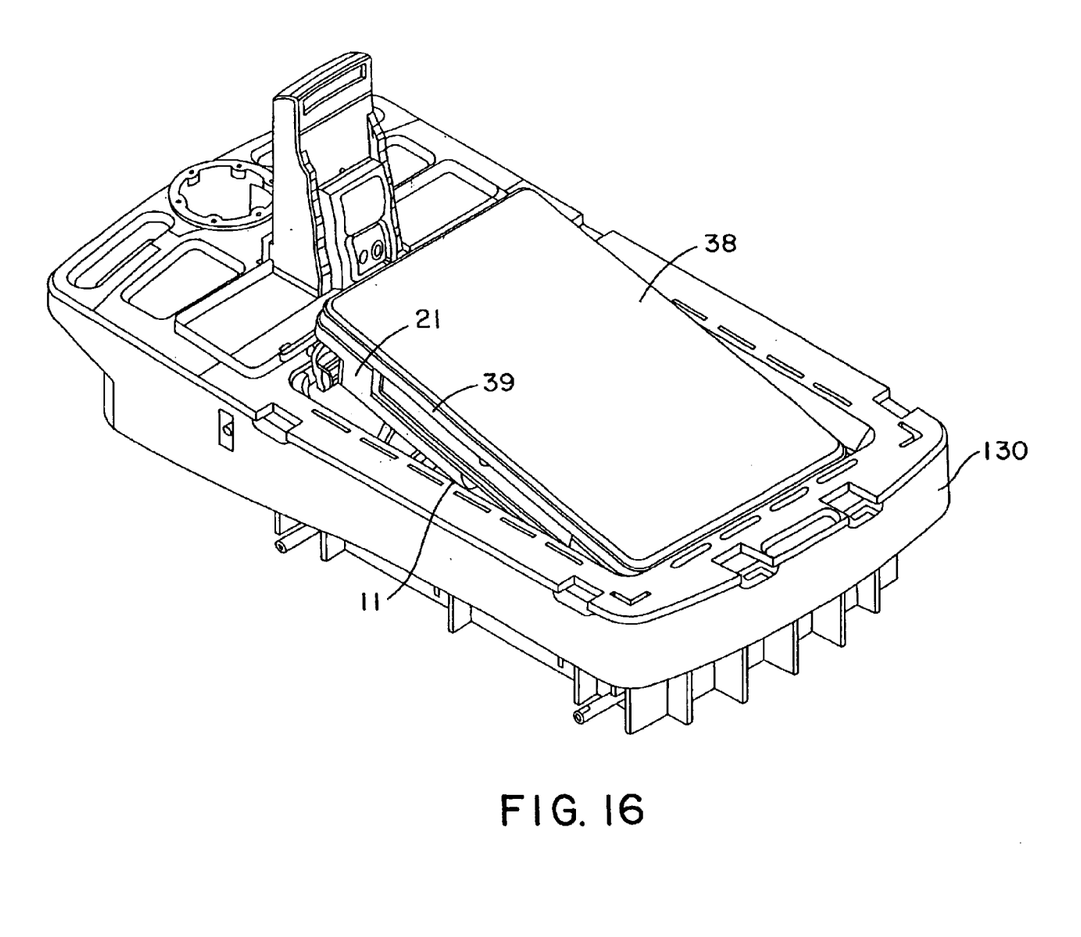
FIG. 16 is a perspective view of a portion of the infant support apparatus of FIG. 1 showing the deck in the Trendelenberg tilt position similar to FIG. 12.

A slide bracket 24 attached to first end 22 by mechanical fasteners 25 movably engages first rail 19 along its longitudinal axis. Slide bracket 24 is configured to move longitudinally and transversely with respect to first rail 19 as shown in FIGS. 12 and 13. In the illustrated embodiment, slide bracket 24 includes slide block 45 which defines a bearing surface that engages rail 19. It is appreciated that slide block 45 may be attached to slide bracket 24 by any conventional means, including, but not limited to bolts 45', adhesives (not shown), or may be an integral component of the slide bracket (not shown). It is also appreciated that any suitable bearing surface can be associated with slide bracket 24 to facilitate movement, such as a ball bearing assembly or wheel assembly. On end 23 opposite bracket 24 is pivot mount assembly 28. Slide bracket 24 and pivot mount assembly 28 move in concert laterally between first and second stops 52, 53 on rails 19, 20, respectively. (See FIG. 11.)

The illustrative operation of deck 21 with respect to apparatus 120 is shown in FIGS. 2 through 7. Specifically regarding the movement of deck 21, as shown in FIGS. 6, 7 and 17, the care giver may grasp either side of deck 21 or mattress 38. By applying either a pushing or pulling force on deck 21, the care giver may cause bracket 24 and assembly 28 to slide along rails, 19, 20, respectively. Accordingly, lateral movement is established. The care giver is, thus, free to move deck 21 between the central and extended positions. The extent of lateral movement to the extended position is illustratively limited by stops 52, 53 positioned at the ends of rails 19, 20, respectively. (See FIG. 11.) Because, block 24 and assembly 28 are each positioned at about half the width of first and second ends 22, 23 of deck 21, respectively, (see FIG. 13) the maximum lateral distance deck 21 may travel, which defines the extended position, is approximately one half the width of deck 21. It is contemplated, however, that block 24 and assembly 28 may be positioned anywhere along either ends 22, 23 to allow greater or lesser lateral movement of deck 21 depending on the needs of the care giver.

It will be appreciated that a variety of mechanisms may be used to couple the deck 21 to its support for lateral movement in either or both directions away from its central position shown in FIGS. 2–7. These mechanisms may include slides, rails, rollers or other types of well known movable suports. The deck 21 may move any desired lateral distance away from its central position. The side panels 144 may be lowered to permit such movement laterally.

To move deck 21 between Trendelenberg and reverse-Trendelenberg tilt positions, the care giver may engage either mechanism 15 or 16 to change the height of deck 21 relative to tub 130. For example, if the care giver raises mechanism 16, as shown in FIG. 12, deck 21 will move to the Trendelenberg position. Conversely, if mechanism 15 is raised and mechanism 16 is lowered, deck 21 will move to the reverse-Trendelenberg position. Cavity 14 is configured to receive a portion of deck 21 when in such positions.

Accordingly, slide bracket 24 is also configured to move radially with respect to the longitudinal axis of first rail 19 to compensate for movement of deck 21 between Trendelenberg and reverse-Trendelenberg tilt positions. Specifically, slide bracket 24 compensates for the relative change in distance between rails 19, 20 that result from such movement. For example, when second end 23 Trendelenberg tilts, the distance between rails 19, 20 increases by distance 5 as shown in FIG. 12, similar to the hypotenuse of a triangle. In the illustrated embodiment, a slide stop 26 is attached to bracket 24 to limit such radial movement of bracket 24 with respect to first rail 19 thus preventing first rail 19 from detaching. It is appreciated that slide stop 26 can be attached to slide bracket 24 by any conventional means, including, but not limited to, a bolt 27, an adhesive (not shown), or can be an integral component of the slide bracket itself (not shown).

Pivot mount assembly 28 is provided on end 23 and pivots about rail 20 to allow movement to the Trendelenberg and reverse-Trendelenberg tilt positions. An exploded view of pivot mount assembly 28 is shown in FIG. 13. Assembly 28 is configured to pivot about the longitudinal axis of second rail 20 as the height of mechanisms 15 and/or 16 changes as shown in FIG. 12, as previously discussed. (See also FIGS. 12 and 18.) A latch 33 is also provided to removably attach deck 21 to assembly 28. In the illustrated embodiment, a latch pin 29 extends from pivot mount assembly 28. A latch plate 30 is affixed to assembly 28 and includes an aperture 31 disposed there through and sized to receive latch pin 29. Latch plate 30 is configured to cooperate with opening 32 and is disposed there through to provide a generally flush surface between itself and deck 21. (See FIG. 14.)

Latch plate 30 also includes a stepped structure 47, formed about the perimeter of deck aperture 32, that corresponds to a stepped structure 47' formed about the perimeter of latch plate 30, as shown in FIG. 9. Latch pin 29 extends through aperture 31 in latch plate 30 and is secured by latch clamp 50 of latch 33. A rivet 34 is movable along rivet opening 51 which is disposed through latch 33 and, in conjunction with guide 46, restricts latch 33 to only linear movement. Latch 33 is configured to slidably secure to latch plate 30 by clipping to or friction-fitting to pin 29 and rivet 34, thereby coupling plate 30 and, thus, assembly 28 to deck 21. This allows convenient engagement and disengagement of clamp 50 to latch pin 29.

If the care giver desires to remove deck 21 from rails 19, 20, the care giver will grasp latch 33 and slide it away to disengage latch 33 from pin 29 and rivet 34. If the care giver removes slide stop 26 from bracket 24, the care giver is free to lift deck 21 upwardly causing it to disengage from better assembly 28 at end 23 and rail 19 at end 22. To replace deck 22 onto rails 19 and 20, the care giver will engage rail 19 with bracket 24 and re-attach stop 26, mate aperture 32 with plate 30 and then couple latch 33 to pin 29 and rivet 34.

Although the foregoing apparatus has been described, one skilled in the art can easily ascertain the essential characteristics of the apparatus, and various changes and modifications may be made to adapt the various uses and characteristics without departing from the spirit and scope of this disclosure, as described by the claims which follow.

What is claimed is:

1. An infant support apparatus comprising:
   a frame;
   a deck carried by the frame, the deck being mounted on the frame for selective movement relative to the frame between a first position, a second position and a third position, the first position being substantially centered on the frame, the second position being located laterally on one side of the first position, the third position being located laterally on the opposite side of the first position from the second position; and
   a mattress coupled to the deck for lateral movement with the deck relative to the frame.

2. The apparatus of claim 1, wherein the deck further comprises spaced apart first and second ends.

3. The apparatus of claim 2, wherein the first end includes a first slide assembly and wherein the second end includes a second slide assembly.

4. The apparatus of claim 3, wherein the first and second slide assemblies further comprise first and second sliding surfaces, respectively, and the deck further comprises first and second slide blocks configured to engage the first and second sliding surfaces, respectively, to allow movement of the deck relative to the frame.

5. The apparatus of claim 4, wherein the first and second sliding surfaces are rails.

6. The apparatus of claim 1, further comprising a weldment attached to the deck.

7. The apparatus of claim 1, wherein the frame includes laterally spaced apart first and second end walls provided adjacent first and second side walls to define a cavity, and wherein the deck substantially occludes the cavity when the deck is in the central position and allows access to the cavity when moved to the laterally extended position.

8. The apparatus of claim 1 additionally comprising a weight scale coupled to the deck.

9. An infant support apparatus comprising:
   a frame;
   a deck carried by the frame, the deck being mounted to the frame for movement relative to the frame between a first position and a second position laterally spaced apart from the first position; and
   a weight scale coupled to the deck,
   wherein the deck further comprises spaced apart first and second ends,
   wherein the first end includes a first slide assembly and wherein the second end includes a second slide assembly,
   wherein the first and second slide assemblies further comprise first and second sliding surfaces, respectively, and the deck further comprises first and second slide blocks configured to engage the first and second sliding surfaces, respectively, to allow movement of the deck relative to the frame, and wherein the first and second slide assemblies are movable in a direction non-parallel to the lateral movement of the deck.

10. The apparatus of claim 9, wherein the first and second slide assemblies are movable between Trendelenburg and reverse-Trendelenburg tilt positions.

11. The apparatus of claim 9, wherein the first slide block is detachable from the deck.

12. The apparatus of claim 11, wherein the second slide block is removably attached to the deck.

13. An infant support apparatus comprising:
   a frame;
   a deck carried by the frame, the deck being mounted to the frame for movement relative to the frame between a first position and a second position laterally spaced apart from the first position; and
   an x-ray cassette coupled to the deck.

14. The apparatus of claim 13, wherein the deck further comprises spaced apart first and second ends.

15. The apparatus of claim 14, wherein the first end includes a first slide assembly and wherein the second end includes a second slide assembly.

16. The apparatus of claim 15, wherein the first and second slide assemblies further comprise first and second sliding surfaces, respectively, and the deck further comprises first and second slide blocks configured to engage the first and second sliding surfaces, respectively, to allow movement of the deck relative to the frame.

17. The apparatus of claim 15, wherein the first and second sliding surfaces are rails.

18. The apparatus of claim 17, wherein the first and second slide assemblies are movable in a direction non-parallel to the lateral movement of the deck.

19. The apparatus of claim 18, wherein the first and second slide assemblies are movable between Trendelenburg and reverse-Trendelenburg tilt positions.

20. The apparatus of claim 18, wherein the first slide block is detachable from the deck.

21. The apparatus of claim 20, wherein the second slide block is removably attached to the deck.

22. The apparatus of claim 13, further comprising a weldment attached to the deck.

23. The apparatus of claim 13, wherein the frame includes laterally spaced apart first and second end walls provided adjacent first and second side walls to define a cavity, and wherein the deck substantially occludes the cavity when the deck is in the central position and allows access to the cavity when moved to the laterally extended position.

24. An infant support apparatus for an incubator or warmer, the apparatus comprising:
   a base,
   a support configured to receive an infant, the support being movable up upwardly and downwardly relative to the base and being movable laterally between a central position and a position spaced therefrom;
   side guards associated with the support, the side guards being movable between upright and lowered positions and configured to provide access to the infant; and
   an assembly comprising a canopy and radiant warmer;
   the assembly being movable upwardly and downwardly relative to the support between upper and lower positions;

the assembly being in the lower position, the canopy cooperates with the aide guards, in the upright position, to form an incubator enclosure configured to receive the infant; and the assembly being in the upper position, the radiant warmer is configured to direct radiant heat to the infant.

25. The apparatus of claim 24, comprising a humidifier for providing moist air to the enclosure.

26. The apparatus of claim 24, comprising an x-ray tray under the support surface for x-raying the infant.

27. The apparatus of claim 24, comprising one or more weight scales coupled to the support for monitoring the weight of the infant.

28. The apparatus of claim 24, in which the support includes a head end and a foot end spaced-apart from the head end, the assembly comprising a canopy support at the head end, the canopy support being provided to raise and lower the canopy and radiant warmer relative to the support.

29. The apparatus of claim 24, further comprising a canopy support at one end of the support, the canopy and radiant warmer assembly being movable on the canopy support between its upper and lower positions.

30. The apparatus of claim 29, comprising a motor associated with the support configured to raise and lower the assembly.

31. The apparatus of claim 24, wherein the side guards are pivotable in a direction away from the support to provide access to the infant.

* * * * *